(12) United States Patent  (10) Patent No.: US 8,273,088 B2
Zalenski et al.  (45) Date of Patent: Sep. 25, 2012

(54) BONE REMOVAL TOOL

(75) Inventors: Edward Zalenski, Lakeville, MA (US); Jeffrey Karl Sutton, Medway, MA (US)

(73) Assignee: DePuy Spine, Inc., Raynham, MA (US)

( * ) Notice: Subject to any disclaimer, the term of this patent is extended or adjusted under 35 U.S.C. 154(b) by 1481 days.

(21) Appl. No.: 11/177,627

(22) Filed: Jul. 8, 2005

(65) Prior Publication Data

US 2007/0010822 A1   Jan. 11, 2007

(51) Int. Cl.
*A61B 17/00* (2006.01)
(52) U.S. Cl. ............... 606/84; 606/79; 606/80; 606/279
(58) Field of Classification Search .................. 606/279, 606/79–85; 407/29.14
See application file for complete search history.

(56) References Cited

U.S. PATENT DOCUMENTS

| | | |
|---|---|---|
| 4,993,410 A | 2/1991 | Kimsey |
| 5,019,103 A | 5/1991 | Van Zile |
| 5,019,108 A | 5/1991 | Bertin |
| 5,041,117 A | 8/1991 | Engelhardt |
| 5,064,426 A | 11/1991 | Huebsch |
| 5,163,519 A | 11/1992 | Mead |
| 5,188,531 A | 2/1993 | Von Sutfin |
| 5,236,358 A | 8/1993 | Sieffert |
| 5,324,292 A | 6/1994 | Meyers |
| 5,382,251 A | 1/1995 | Hood |
| 5,472,452 A | 12/1995 | Trott |
| 5,484,437 A * | 1/1996 | Michelson ................ 606/86 A |
| 5,500,001 A | 3/1996 | Trott |
| 5,527,343 A | 6/1996 | Bonutti |
| 5,536,266 A | 7/1996 | Young |
| 5,609,595 A | 3/1997 | Pennig |
| 5,697,837 A | 12/1997 | Verrijp |
| 5,733,289 A | 3/1998 | Seedhom |
| 5,749,877 A | 5/1998 | Young |
| 5,759,185 A | 6/1998 | Grinberg |
| 5,782,636 A | 7/1998 | Armstrong |
| 5,782,835 A | 7/1998 | Hart |
| 5,797,917 A | 8/1998 | Boyd |
| 5,851,209 A | 12/1998 | Kummer |
| 5,891,149 A | 4/1999 | Young |
| 6,017,348 A | 1/2000 | Hart |
| 6,033,407 A | 3/2000 | Behrens |
| 6,083,228 A | 7/2000 | Michelson |
| 6,095,913 A | 8/2000 | Peat |
| 6,126,535 A | 10/2000 | Post |
| 6,139,551 A | 10/2000 | Michelson |
| RE37,005 E | 12/2000 | Michelson |
| 6,187,012 B1 | 2/2001 | Masini |
| 6,190,392 B1 | 2/2001 | Vandewalle |
| 6,224,596 B1 | 5/2001 | Jackson |
| 6,224,607 B1 * | 5/2001 | Michelson ................ 606/96 |
| 6,264,660 B1 | 7/2001 | Schmidt |

(Continued)

OTHER PUBLICATIONS

Discount-Tools.com, Rotary Files—Burrs, accessed through http://web.archive.org on Jul. 20, 2009, available online Oct. 12, 2004.*

*Primary Examiner* — Eduardo C Robert
*Assistant Examiner* — Julianna N Harvey

(57) ABSTRACT

A bone preparation device for preparing a bone surface for receiving an implant is disclosed, as is a method of using the device, wherein the device contains a gripping element for gripping a first bone surface and a abrading element for abrading an opposing bone surface.

14 Claims, 7 Drawing Sheets

U.S. PATENT DOCUMENTS

| | | |
|---|---|---|
| 6,270,501 B1 | 8/2001 | Freiberg |
| 6,331,179 B1 | 12/2001 | Freid |
| 6,358,253 B1 | 3/2002 | Torrie |
| 6,503,253 B1 | 1/2003 | Fletcher |
| 6,582,439 B1 | 6/2003 | Sproul |
| 6,599,290 B2 | 7/2003 | Bailey |
| 6,608,628 B1 | 8/2003 | Ross |
| 6,610,067 B2 | 8/2003 | Tallarida |
| 6,652,533 B2 | 11/2003 | O'Neil |
| 6,656,187 B1 | 12/2003 | Camino |
| 6,682,535 B2 | 1/2004 | Hoogland |
| 6,702,823 B2 | 3/2004 | Iaia |
| 6,706,072 B2 | 3/2004 | Dwyer |
| 6,723,101 B2 | 4/2004 | Fletcher |
| 6,733,292 B2 | 5/2004 | Odrich |
| 6,783,532 B2 | 8/2004 | Steiner |
| 2002/0004660 A1 | 1/2002 | Henniges |
| 2002/0045898 A1 | 4/2002 | Freid |
| 2002/0055713 A1 | 5/2002 | Gibbs |
| 2002/0058945 A1 | 5/2002 | Steiner |
| 2002/0058949 A1 | 5/2002 | Iaia |
| 2002/0058999 A1 | 5/2002 | Dwyer |
| 2002/0068941 A1* | 6/2002 | Hanson et al. ............ 606/79 |
| 2002/0072805 A1 | 6/2002 | Sullivan |
| 2002/0091387 A1 | 7/2002 | Hoogland |
| 2002/0091393 A1 | 7/2002 | Gundlapalli |
| 2002/0116023 A1 | 8/2002 | Fletcher |
| 2002/0133159 A1 | 9/2002 | Jackson |
| 2002/0147498 A1 | 10/2002 | Tallarida |
| 2003/0028197 A1 | 2/2003 | Hanson |
| 2003/0055434 A1 | 3/2003 | O'Neil |
| 2003/0125746 A1 | 7/2003 | Sproul |
| 2003/0125810 A1 | 7/2003 | Sullivan |
| 2003/0135277 A1 | 7/2003 | Bryan |
| 2003/0153921 A1 | 8/2003 | Stewart |
| 2003/0158556 A1 | 8/2003 | Taras |
| 2003/0236521 A1 | 12/2003 | Brown |
| 2003/0236522 A1 | 12/2003 | Long |
| 2003/0236525 A1 | 12/2003 | Vendrely |
| 2004/0015170 A1 | 1/2004 | Tallarida |
| 2004/0127897 A1 | 7/2004 | Freid |
| 2004/0142651 A1 | 7/2004 | Jensen |
| 2004/0153078 A1 | 8/2004 | Grinberg |
| 2004/0167523 A1 | 8/2004 | Jackson |
| 2004/0167525 A1 | 8/2004 | Jackson |
| 2004/0167526 A1 | 8/2004 | Jackson |
| 2004/0199167 A1 | 10/2004 | Fletcher |
| 2004/0267257 A1* | 12/2004 | Bourne et al. ............ 606/41 |

* cited by examiner

BONE REMOVAL TOOL

FIELD OF THE INVENTION

The present invention relates to instruments and methods used in surgery. More particularly, the present invention relates to instruments for removing bone and cartilage as well as methods for preparing bone surfaces for receiving an implant.

BACKGROUND OF THE INVENTION

Chronic back problems can cause pain and disability. Frequently, the cause of the back pain is due to a diseased disc located between two vertebral bodies. The disc becomes diseased or degenerated resulting in a decrease in space between the vertebral bodies, which may result in persistent pain. Surgical procedures have been developed to replace the damaged disc with an implant between the two vertebral bodies to restore the height between them. The implant can either be a fusion device, which fuses the vertebrae together or an artificial disc, which restores the motion between the vertebrae. Whether it is a fusion device or an artificial disc, surgical insertion of the implant requires preparation of the opposing bone surfaces or endplates of the vertebral bodies. The ease of use and efficiency of the instruments and procedures used to prepare and place an implant between the vertebral bodies is critical to the success of the procedure.

In the current state of the art, hand-held chisels and rasps, or powered devices, such as burrs, are used to prepare the vertebral endplate for receiving an implant. These devices are awkward and sometimes ineffective or overly aggressive in removing too much bone. In the case of powered devices, there are safety concerns when driving forces are directed towards the spinal cord or nerve roots. Typically, the conventional instruments have tips wherein the abrading element are located on the inferior and superior surfaces of the tips. The instruments are inserted between the vertebral bodies and either maneuvered by hand or power. When used manually, the surgeon pushes and pulls the instrument towards and away from him or her, cutting the endplates in an anterior-posterior direction. Often times, the instrument has to be repositioned and this motion repeated to cover the entire surface area needing to be prepared to receive the implant. Other instruments are pivoted and swept from side-to-side (like a windshield wiper) to prepare the entire surface area for the implant. This can be difficult due to the size and shape of the tip and the natural contouring of the endplate. The tip can become difficult to maneuver in the tight space. When power is used, the abrading element of the instrument moves independent of the shaft and can be overly aggressive in removing bone.

A need is present for an instrument that removes bone and cartilage in a controlled manner to prepare a bone surface for receiving an implant.

SUMMARY OF THE INVENTION

The present invention is directed to an instrument for removing bone and cartilage and methods that provide efficient and precise preparation of a bone surface for receiving an implant.

According to a first aspect of the invention, there is provided a bone removal device for preparing a bone surface for receiving an implant, comprising:
 a) a body having an opening extending along a longitudinal axis,
 b) a moveable shaft adapted to move within the opening of the body comprising:
  i) a proximal end portion,
  ii) a distal end portion,
  iii) an outer surface, and
  iv) an abrading element disposed upon approximately 50 percent or less of the outer surface of the distal end portion of the shaft.

According to a first aspect of the invention, there is provided a bone preparation device comprising:
 a) a shaft extending from a proximal end portion to a distal end portion along a longitudinal axis;
 b) a generally cylindrical shaped tip having an outer surface and connected to the distal end portion of the shaft; and
 c) an abrading element disposed upon a first portion of the outer surface of the tip.

BRIEF DESCRIPTION OF THE FIGURES

These and other features and advantages of the present invention will be more fully understood by reference to the following detailed description in conjunction with the attached drawings in which like reference numerals refer to like elements through the different views. The drawings illustrate principals of the invention and, although not to scale, show relative dimensions.

DETAILED DESCRIPTION OF THE INVENTION

The present invention provides an instrument for removing bone and cartilage or other tissue to prepare the bone surface for receiving an implant. The present invention will be described below relative to an illustrative embodiment. Those skilled in the art will appreciate that the present invention may be implemented in a number of different applications and embodiments and is not specifically limited in its application to the particular embodiments depicted herein.

The bone removal instrument of an illustrative embodiment of the invention may be used in spinal surgery, for example, during a spinal fusion or disc replacement procedure to prepare the vertebral endplates for placement of the implant, though one skilled in the art will recognize that the invention can be used with any implant in any surgical procedure that requires preparation of a bone surface.

Figure 1:
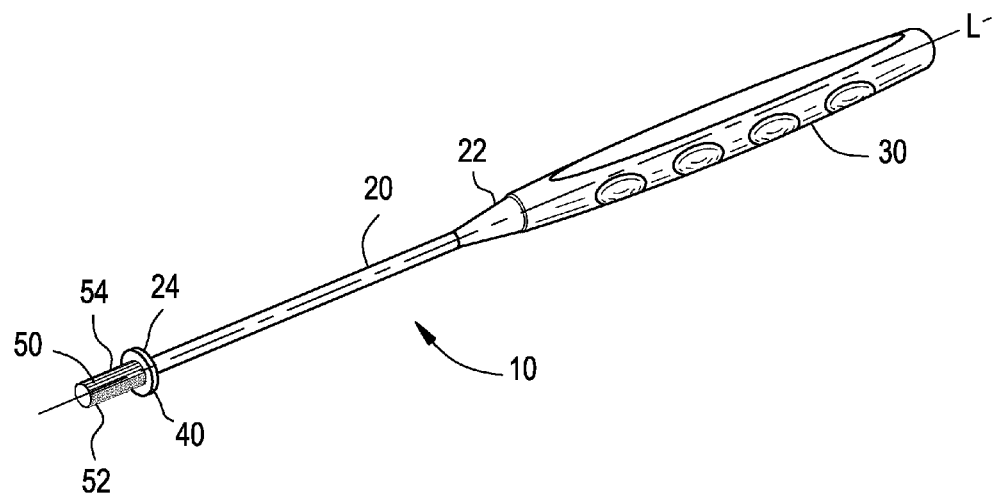
FIG. 1 illustrates a bone removal instrument according to an embodiment of the invention.

Referring to FIG. 1, a bone removal instrument 10 is shown that prepares the bone surface for receiving an implant. The illustrative instrument 10 includes a shaft 20 and a handle 30 extending from the shaft. The handle may be formed from the same material as the shaft and further include texturing such as dimples, ridges or roughening for gripping purposes or may be formed from a soft covering capable of providing a secure grip. Those of ordinary skill in the art will recognize that there are many types of handle configurations and materials adapted to provide a secure grip.

The instrument 10 has a shaft 20 extending along a longitudinal axis having a proximal end portion 22 and distal end portion 24. Handle 30 extends from the proximal end portion of the shaft. A bone preparation tip 50 extends from the shaft at the distal end portion 24. In the illustrated embodiment, the tip 50 also extends along a longitudinal axis and has a generally cylindrical shape. The outer surface 52 of the tip has an abrading element 54. In one embodiment, shown in FIG. 2 the abrading element may be in the form of a knurl pattern 56 capable of abrading or cutting. An example of a knurl capable of cutting is a medium diamond knurl. Other examples include scallop, semi-circular, or square shaped patterns. In another embodiment as shown in FIG. 3, the abrading element may be in the form of cutting flutes 58 extending longitudinally from the distal to the proximal end of the tip. In some embodiments the abrading elements are oriented such that they only abrade in one direction. For example, the abrading element may only cut in a clockwise or counterclockwise direction when the shaft is rotated about its longitudinal axis. The abrading elements may cover a portion of the outer surface or the entire outer surface of the tip.

Figure 2:
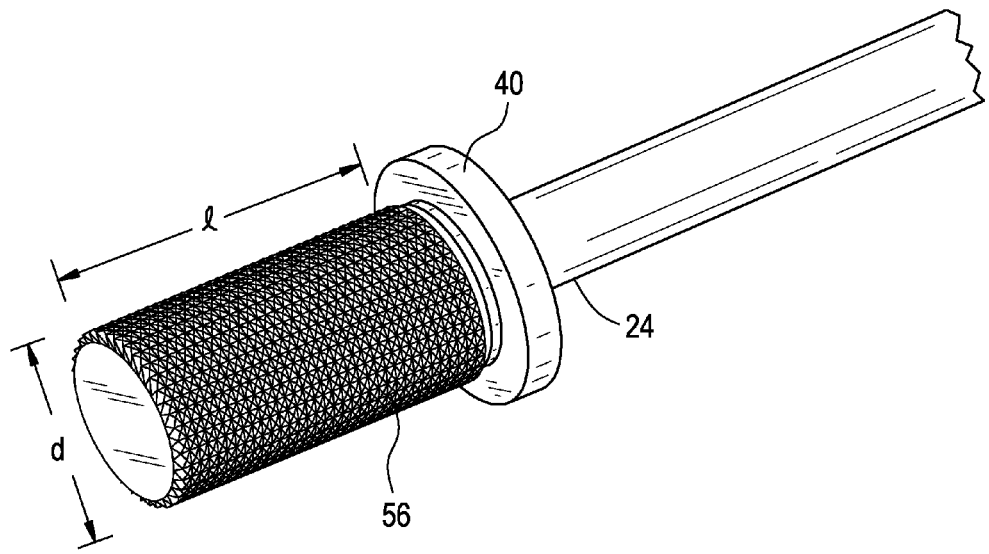
FIG. 2 illustrates a perspective view of the tip and distal end of the shaft of the instrument shown in FIG. 1.
Figure 3:
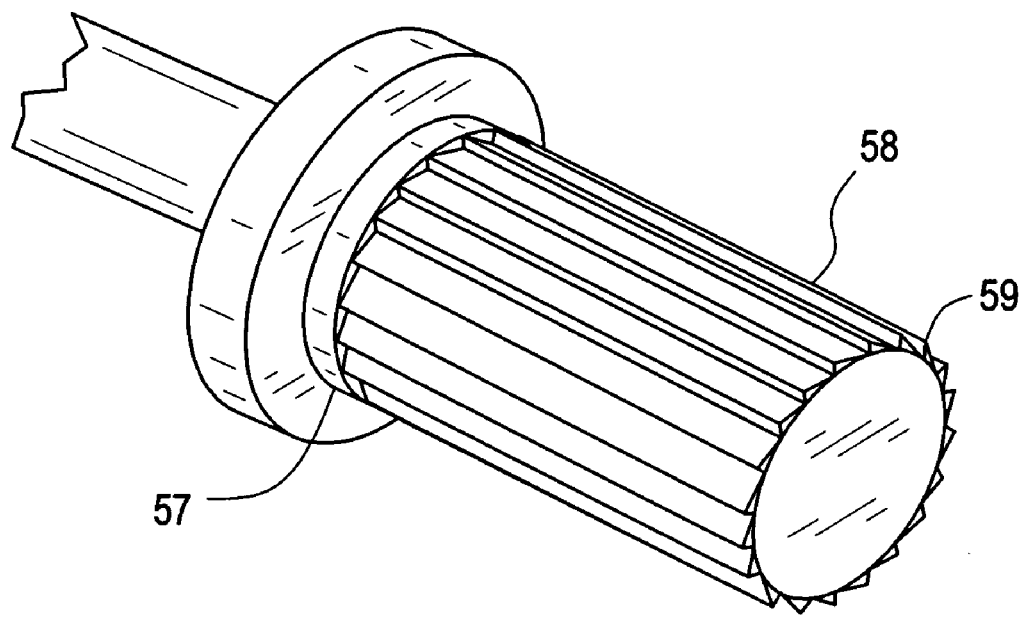
FIG. 3 illustrates an alternate embodiment of the tip of the instrument shown in the FIG. 1.

As illustrated in FIG. 2 the tip 50 has a length l that extends along the longitudinal axis and a diameter d. The length and diameter of the tip corresponds to the respective length, in the anterior-posterior direction, and height of the implant to be placed. Multiple tips may be included in a set corresponding to the same size of the implants available. The tips may be permanently attached to the shaft using any known fastening technique including welding, brazing, adhesives, etc. Alternately, the tip may be removably secured to the shaft using any known fastening techniques including threading, friction, set screws, etc. By providing modular tips, only one shaft need be provided with multiple tips reflective of the range of implants available. Preferably, the instrument is made from surgical stainless steel, however other biocompatible materials meeting the strength requirements may also be used.

Figure 4A:
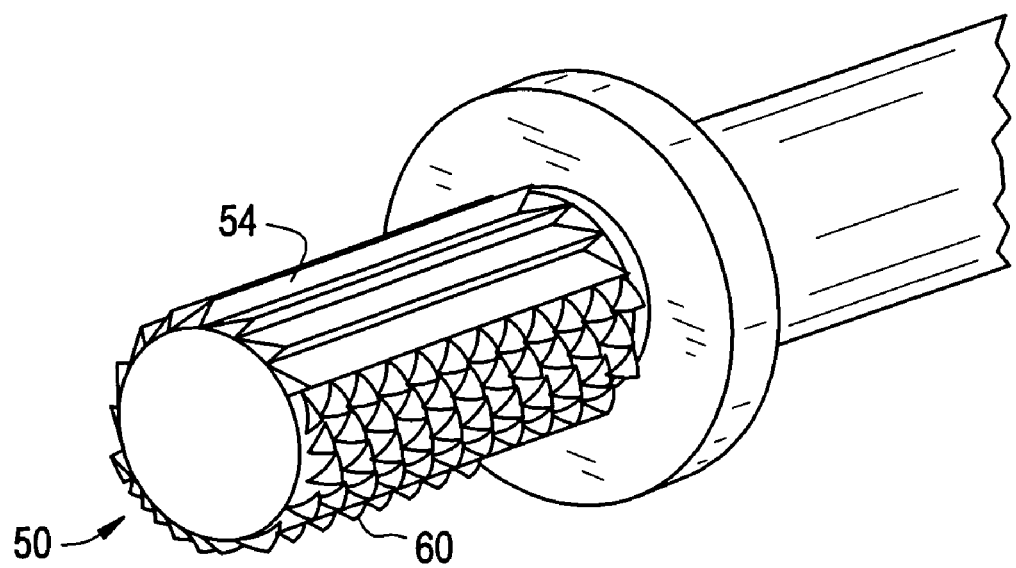
FIG. 4A illustrates another embodiment of the invention including a tip having abrading and gripping elements.
Figure 4B:
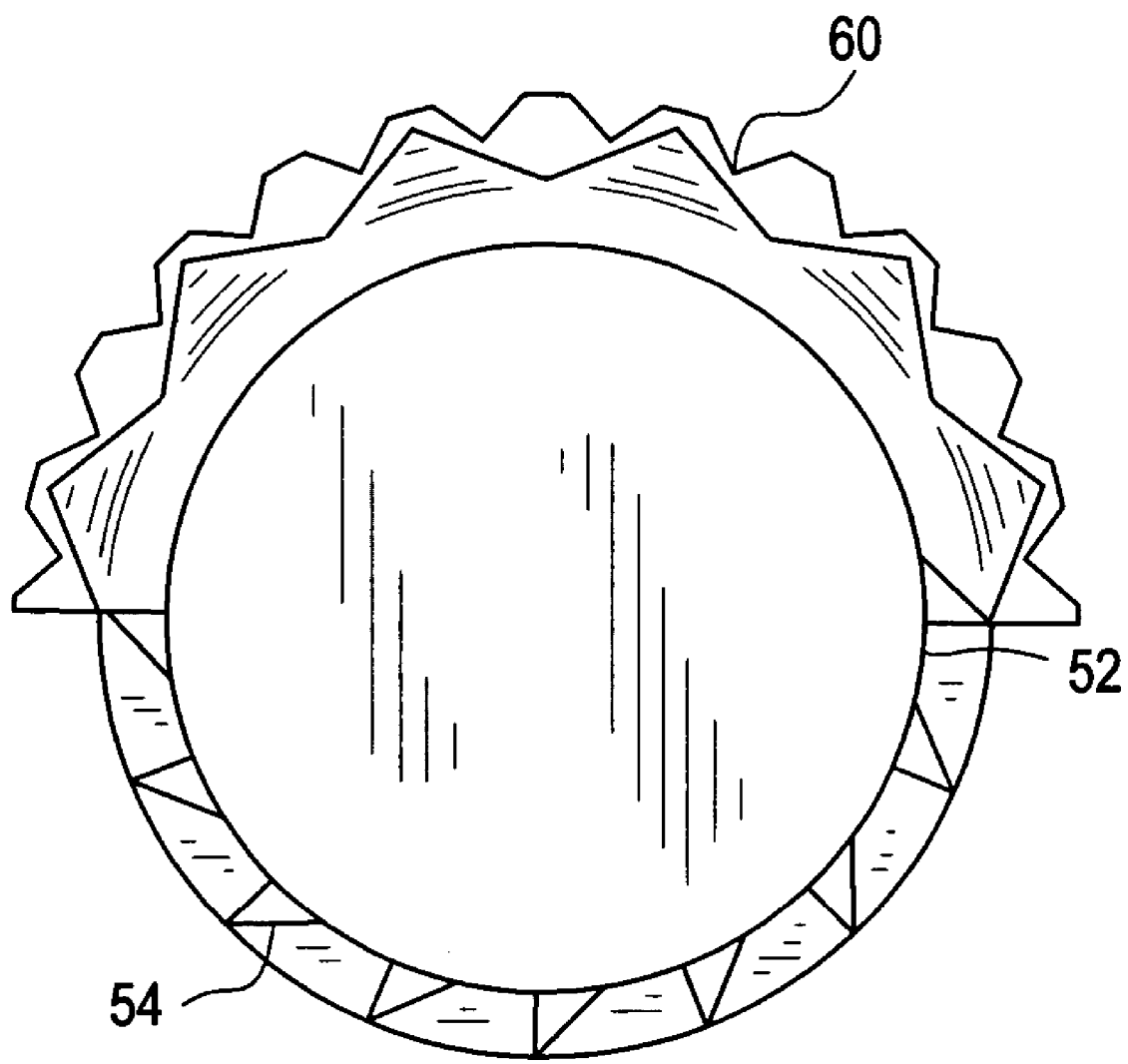
FIG. 4B illustrates one configuration of the tip on the instrument shown in FIG. 4A.

In an alternate embodiment, shown in FIGS. 4A-B, the tip 50 may have an abrading element 54 upon a first portion of the outer surface 52 and a gripping element 60 around a second portion of the outer surface. In one exemplary embodiment, the abrading element may be located around approximately 180 degrees of the outer surface of the tip and the gripping element may be located around the remaining approximately 180 degrees of the outer surface of the tip. In other exemplary embodiments, the abrading element may extend over more than 180 degrees of the outer surface and the gripping element may extend over less than 180 degrees, or vice-versa. In another embodiment, the gripping element and the abrading element extend over the entire axial length of the tip from the proximal to the distal end.

The gripping element 60 is adapted to grip, but not cut or abrade, the bony surface it contacts. It may have a texturing or coating of the surface that does not cut such as knurls, etchings, grooves, ridges, a porous coating or foam coating, or any other pattern suitable for gripping. In another embodiment, the gripping surface may be coated with a polymer having a tacky characteristic, such as include silicone, polyester, or polyurethane.

Referring back to FIG. 1, the instrument 10 may further include a stop member 40 disposed circumferentially around the shaft between the distal end portion 24 of the shaft and the proximal end portion of the tip 50 for limiting the insertion depth of the tip. The diameter of the stop is greater than the diameter of the tip such that the stop contacts the anterior face of at least one vertebral body as the tip is inserted into the disc space. The stop may be disposed around 180 degrees or less of the tip.

The instrument of the present invention can be used to prepare a bone surface for optimal placement of an implant. For exemplary purposes, the method of the invention will be described with respect to preparing the endplates of vertebral bodies for the insertion of a spinal implant such as a fusion device or an artificial disc. However, it will be appreciated that the principles and methods can also be applied to preparing other bone surfaces for implantation of other medical devices. The method of the present invention will be discussed using an anterior approach, where the surgeon seeks access to the spine through the front of the patient. However alternate approaches could include posterior or lateral approaches.

Figure 5:
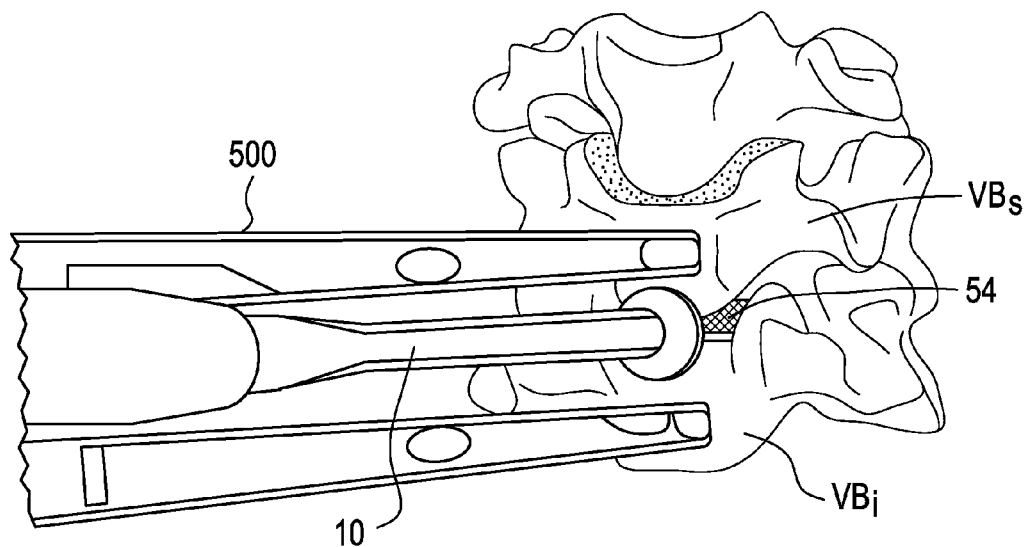
FIG. 5 illustrates the invention shown in FIG. 4A inserted between a distraction instrument.
Figure 6:
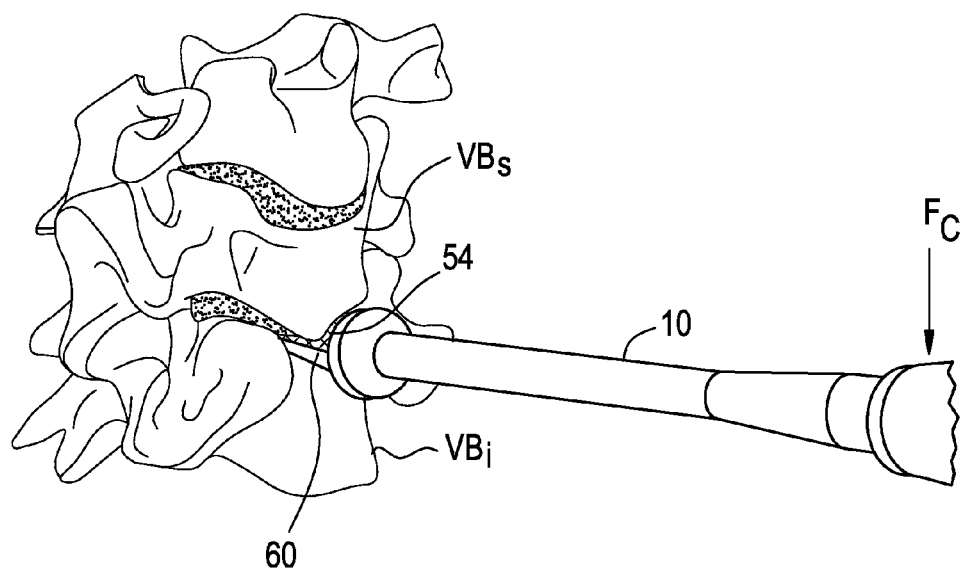
FIG. 6 illustrates the invention inserted between two vertebral bodies under a compressive force.

In a typical surgery to prepare an intervertebral space for receipt of an implant, the surgeon removes the disc between the vertebral bodies where the implant is to be placed. Once the disc is removed, the endplate of the superior vertebrae needs to be prepared for receipt of the implant. If the surgeon is using a distraction instrument 500, as shown in FIG. 5, the bone removal instrument 10 may be inserted through the distraction instrument between the superior vertebral body ($VB_s$) and inferior vertebral body ($VB_i$) with the abrading element positioned to contact the endplate of the superior vertebral body. The distraction may be released or removed as shown in FIG. 6, allowing the superior vertebral body ($VB_s$) to move into contact with the abrading element 54 of the instrument 10. The surgeon exerts a compressive force F, on the handle 30 or shaft 20 of the instrument such that the gripping surface 60 contacts the endplate of the inferior vertebral body ($VB_i$). The surgeon then rotates the shaft approximately 90 degrees in one direction and 90 degrees in the other. The instrument 10 moves from left to right and right to left. The abrading element 54 removes bone and/or cartilage from the superior endplate in a lateral direction and in a controlled manner while the stability of the instrument is insured by the gripping surface. The shape of the inferior endplate is not altered by the gripping surface of the instrument.

Figure 7:
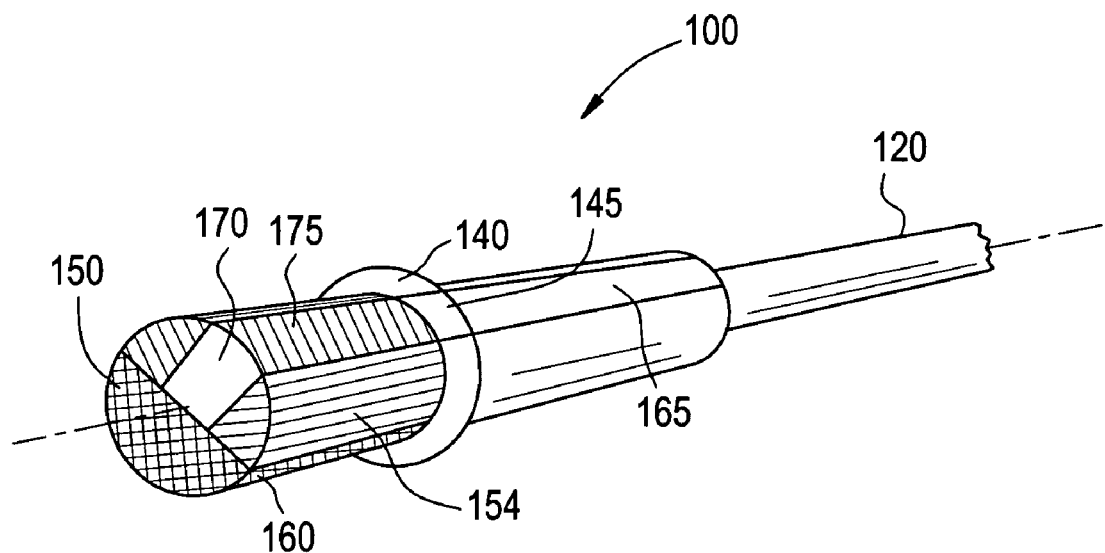
FIG. 7 illustrates an alternate embodiment of the invention.

According to another embodiment, a bone removal instrument 100 illustrated in FIG. 7, includes a shaft 120, having a handle, not shown, at the proximal end, and a tip 150 connected to the distal end portion of the shaft. The tip 150 has a generally cylindrical shape extending from a proximal end to a distal end along a longitudinal axis L. The outer surface of the tip includes an abrading element 154 and a gripping element 160. The tip may further include a movable abrading element 170. The abrading elements may be in the form of a knurl pattern capable of abrading or cutting. An example of a knurl capable of cutting is a medium diamond knurl. Other examples include scallop, semi-circular, or square shaped patterns. In another embodiment, the abrading element may be in the form of cutting flutes extending longitudinally from the distal to the proximal end of the tip. The gripping element may be a texturing or coating of the surface that does not cut such as knurls, etchings, grooves, ridges, a porous coating or foam coating, or any other pattern suitable for gripping. In another embodiment the gripping surface may be coated with a polymer having a tacky characteristic, examples include silicone polyester, or polyurethane. The abrading element 154 covers a first portion of the outer surface of the tip and the gripping element 160 covers a second portion of the outer surface of the tip. The tip may be tapered or shaped to approximate the contour of the bone surface to be prepared.

The movable abrading element 170 extends from the proximal end to the distal end of the tip and is adapted to move parallel to the longitudinal axis of the tip. A separate handle, not shown, extends from the proximal end of the movable abrading element to allow the user to move the abrading element along the longitudinal axis. The movable abrading element has a top, a bottom and two opposing side surfaces. The top surface 175 is capable of cutting or abrading bone or cartilage. The bottom and side surfaces may have features adapted to guide and move the element along the tip. For example, the bottom surface of the moveable abrading element may have a track and the corresponding surface of the tip may have a pin to keep the cutting element moving on the same path. The bottom and side surfaces could also all be smooth to allow a general sliding movement between the cutting element and the tip. The abrading surface has cutting teeth or flutes that cut in an anterior-posterior direction as the element moves along the longitudinal axis of the tip. In another embodiment, the movable abrading element 170 may be angled in such a way to cut only when the cutting element is pulled towards the user, so that the bone fragments will be pulled out of the disc space instead of pushed further inside the space. The abrading element may be angled in any manner to achieve the desired cutting direction.

The instrument may further include a stop 140 around either a portion of the tip or the entire tip to prevent the tip from being advanced too far into the disc space. A stop 145 may also be positioned on the movable abrading element to prevent the abrading element from being advanced too far into the disc space.

Figure 8:
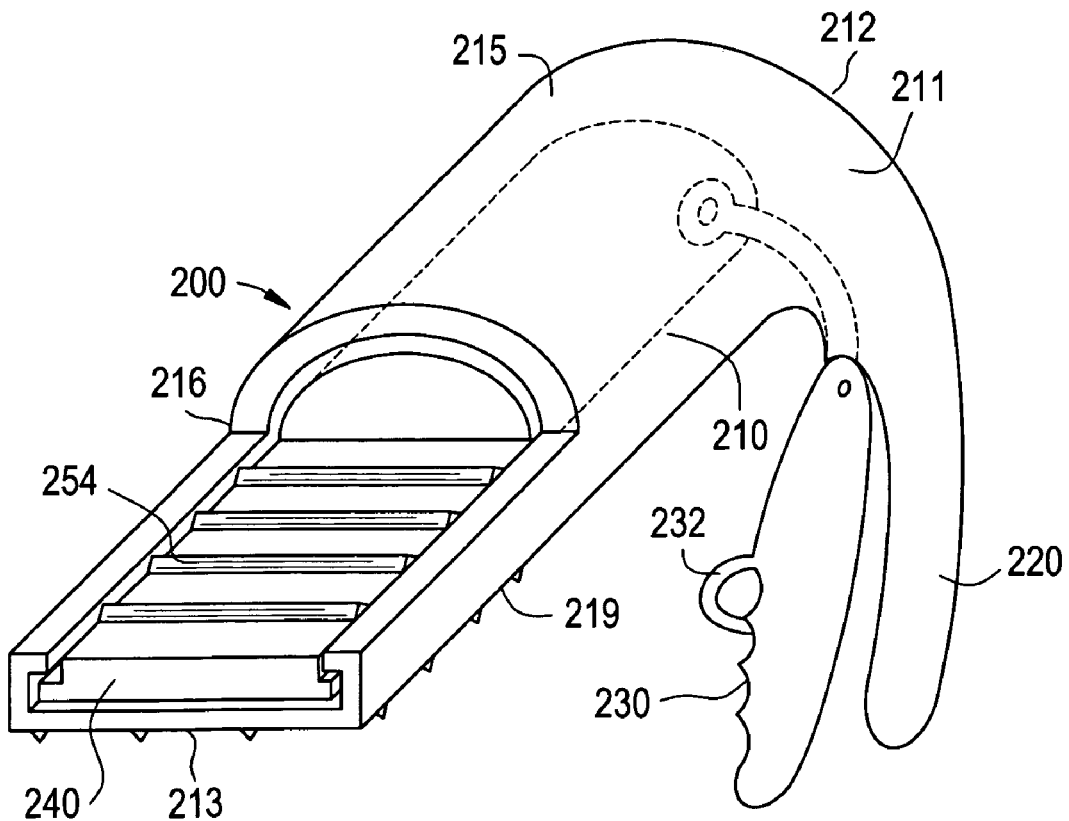
FIG. 8 illustrates another alternate embodiment of the invention.

Another embodiment of a bone removal instrument 200 shown in FIG. 8 has a body 210 connected to a first fixed handle 220, a second handle 230 pivotally connected to the first fixed handle and connected to a sliding shaft 240. The body has a length along a longitudinal axis from a proximal end 211 to a distal end 213. The fixed handle extends from the proximal end of the body. An opening 212 passes through the body from the proximal to the distal end.

The body has a top surface 215 and a bottom surface 217. The top surface has a generally convex shape extending from the proximal end 211 of the body to around a middle portion 216 of the body. The convex outer surface of the body may act as a stop to prevent the instrument from being inserted too far into the disc space. The bottom surface extends from the proximal to the distal end and is generally planar. The bottom surface may have gripping elements 219 on the bottom side extending from around the midportion 216 of the body to the distal end 213. The gripping elements may include surface texturing, coating or polymers having a tacky characteristic. The bottom surface has a track or groove for engaging the sliding shaft. The sliding shaft is connected at its proximal end to the second pivoting handle.

The upper surface of the sliding shaft 240 has an abrading or cutting element 254. The cutting element may be teeth, ridges, flutes, knurls or any other cutting element known to one skilled in the art. As the second handle 230 is engaged, the shaft slides along the groove of the bottom surface of the body. As the sliding shaft advances, the cutting element 254 on the upper surface comes into contact with the superior endplate of the vertebral body. The cutting element prepares the surface by cutting away any bone, tissue or cartilage it contacts. The handle may work in the reverse such that engaging the handle pulls the sliding shaft back into the body of the instrument. Depending on the orientation of the cutting element, the cutting may occur on either the forward movement or the return movement of the sliding shaft.

Figure 9:
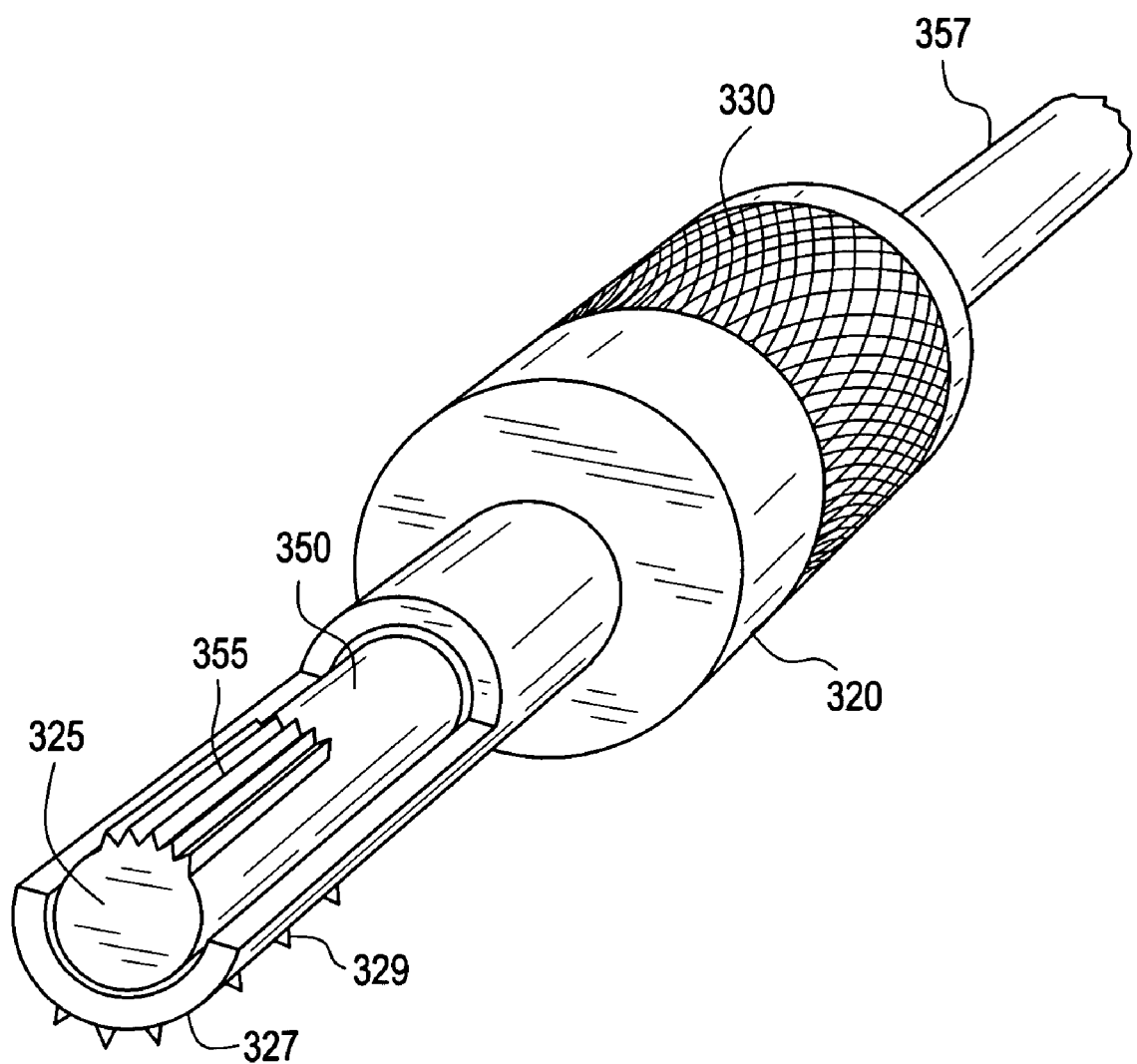
FIG. 9 illustrates an alternate embodiment of the invention.

In another embodiment of the current invention, shown in FIG. 9 the instrument has a body 320 and a movable shaft 350. A handle 330 may be located on the body. The body has a generally cylindrical hollow shape with an opening extending from the proximal to the distal end. The distal portion 325 of the body extends in a semicircular configuration having a bottom surface 327 and an open top surface. A gripping element 329 may be located on the bottom surface such as a texturing or coating of the surface that does not cut such as knurls, etchings, grooves, ridges, a porous coating or foam coating, or any other pattern suitable for gripping. In another embodiment the gripping element may be a coating of a polymer having a tacky characteristic, examples include silicone polyester, or polyurethane.

The movable shaft 350 has a generally cylindrical shape extending through the hollow body. The moveable shaft has abrading or cutting elements 355 around a portion of the outer surface at the distal end. The proximal end 357 of the moveable shaft extends through the body and may have some gripping features to facilitate rotation of the shaft by the user.

Figure 10:
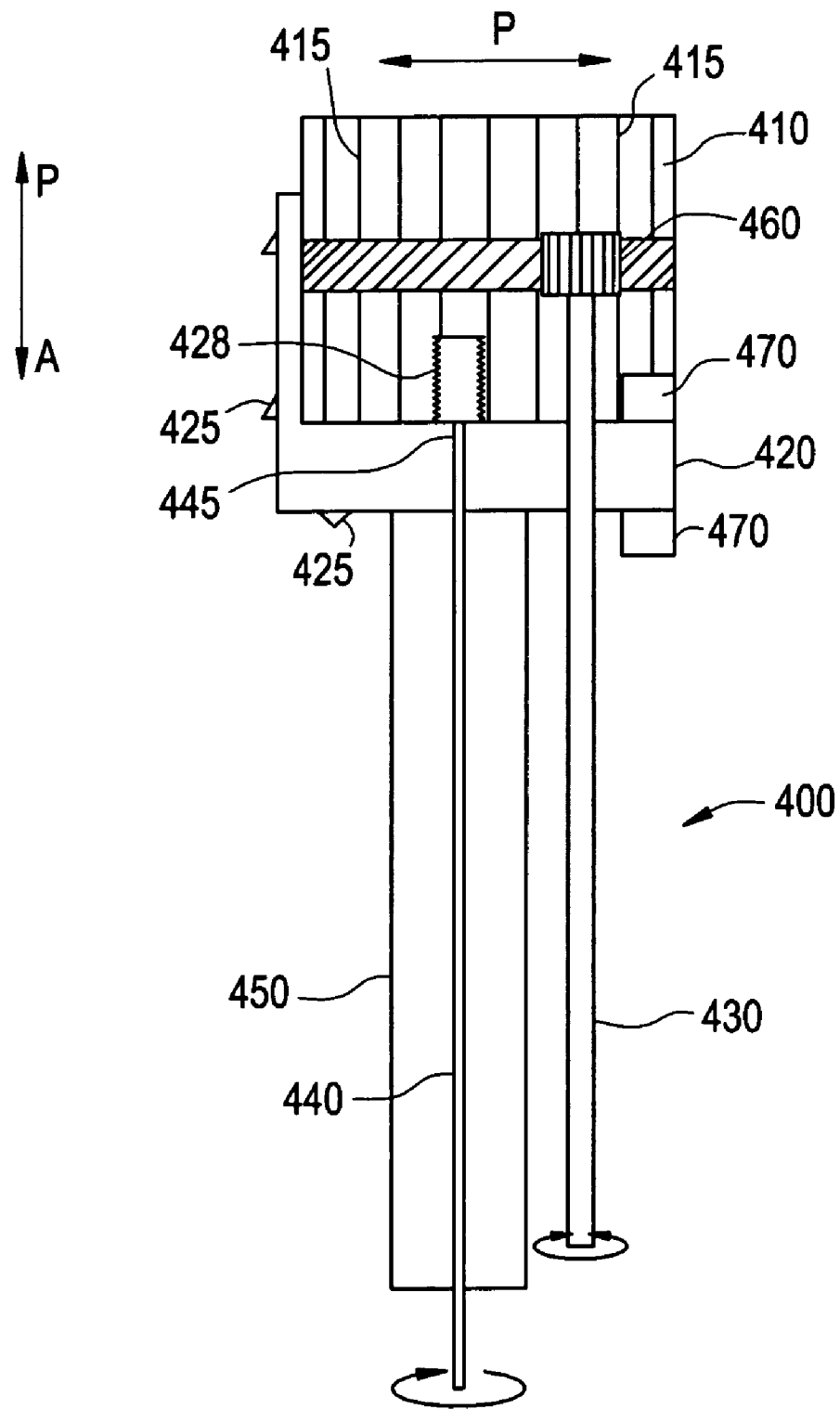
FIG. 10 illustrates an alternate embodiment of the invention.

Another embodiment of a bone removal instrument capable of cutting in a lateral orientation is shown in FIG. 10. The instrument 400 has a superior plate 410, an inferior plate 420, an actuating shaft 430, an adjustment mechanism 440, and a handle 450. The superior plate has a cutting or abrading element 415 on the upper surface. The inferior plate may have a gripping element 425 on the bottom surface. A handle 450 extends from the inferior plate. The inferior and superior plates are engageable with a rack and pinion gear arrangement located between the plates. The inferior plate remains stationary while the superior plate is capable of moving in a direction perpendicular to the longitudinal axis of the handle. The actuating shaft 430 engages the gear to move the superior plate and abrading element in a lateral direction. The adjustment mechanism 440 extends from the superior plate and may include a threaded shaft engageable with a threaded hole on the side of the superior plate. Engagement of the adjustment mechanism allows the superior plate to move in an anterior-posterior direction to provide for better positioning of the instrument within the disc space. The instrument may further include stops 460 to limit the insertion of the instrument. The instrument allows for cutting or abrading of bone and cartilage in a direction perpendicular to the longitudinal axis of the instrument.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense. For example, one skilled in the art will recognize that the instrument of the illustrative embodiment of the invention is not limited to use with spinal implants and can be used with any suitable implant or procedure for any suitable orthopedic system.

It is also to be understood that the following claims are to cover all generic and specific features of the invention described herein, and all statements of the scope of the invention which, as a matter of language, might be said to fall therebetween.

The invention claimed is:

1. A method of preparing a bone surface for receiving an implant with an instrument having a shaft and a generally cylindrical tip, the tip having an outer surface wherein a first portion of the outer surface comprises an abrading element and a remaining portion of the outer surface comprises a gripping element, comprising the steps of:
  a) inserting the gripping element of the tip of the instrument into a disc space;
  b) applying a compressive force on the shaft of the instrument to allow the gripping surface to contact a first bone surface without altering the shape of the first bone surface; and
  c) rotating the shaft about its longitudinal axis such that the abrading element cuts a second bone surface in a direction perpendicular to the longitudinal axis of the shaft,
wherein the cutting of the second bone surface occurs without altering the shape of the first bone surface.

2. The method of claim 1 wherein the step of inserting the instrument further includes applying a distraction force between the two bone surfaces.

3. The method of claim 2 further comprising the step of removing the distraction force.

4. A method of preparing a bone surface for receiving an implant with an instrument having a shaft and a tip, the tip having an outer surface, wherein a first portion of the outer surface comprises an abrading element and a second portion of the outer surface comprises a gripping element, comprising the steps of:
  a) inserting the gripping element of the tip of the instrument into a disc space;
  b) applying a compressive force on the shaft of the instrument so that the gripping element grips a first bone surface without altering the shape of the first bone surface; and
  c) rotating the shaft about its longitudinal axis such that the abrading element cuts a second bone surface,
wherein the cutting of the second bone surface occurs without altering the shape of the first bone surface.

5. The method of claim 4 wherein the abrading element is disposed upon approximately 50 percent or less of the outer surface of the tip.

6. The method of claim 4 wherein the abrading element is located around approximately 180 degrees of the outer surface of the tip and the gripping element is located around the remaining approximately 180 degrees of the outer surface of the tip.

7. The method of claim 4 wherein the abrading element extends over more than 180 degrees of the outer surface and the gripping element extends over less than 180 degrees.

8. The method of claim 4 wherein the abrading element extends over less than 180 degrees of the outer surface and the gripping element extends over more than 180 degrees.

9. The method of claim 4 wherein each of the gripping element and the abrading element extend over an entire axial length of the tip.

10. The method of claim 4 wherein the gripping element contacts only a first bone and the abrading element contacts only a second bone.

11. The method of claim 4 wherein the instrument is inserted between first and second vertebral bodies, and wherein the abrading element contacts an endplate of the first vertebral body, and the gripping element contacts an endplate of a second vertebral body.

12. The method of claim 11 the step of inserting the instrument further includes applying a distraction force between the two endplates, and wherein removal of a distraction force allows the first vertebral body endplate to contact the abrading element.

13. The method of claim 11 wherein exertion of a compressive force on the instrument allows the gripping element to contact the endplate of the second vertebral body.

14. The method of claim 11 wherein the shaft is rotated in a first direction and then rotated in a second direction.

* * * * *